(12) United States Patent
Hanks

(10) Patent No.: US 7,384,265 B2
(45) Date of Patent: Jun. 10, 2008

(54) ORTHODONTIC FORCE MODULE

(76) Inventor: Stephen D. Hanks, 2917 Linkview Dr., Las Vegas, NV (US) 89134

( * ) Notice: Subject to any disclaimer, the term of this patent is extended or adjusted under 35 U.S.C. 154(b) by 0 days.

(21) Appl. No.: 11/440,869

(22) Filed: May 25, 2006

(65) Prior Publication Data

US 2007/0275341 A1    Nov. 29, 2007

(51) Int. Cl.
*A61C 3/00* (2006.01)
(52) U.S. Cl. ......................................................... 433/7
(58) Field of Classification Search .................. 433/7, 433/5, 18
See application file for complete search history.

(56) References Cited

U.S. PATENT DOCUMENTS

| | | | | |
|---|---|---|---|---|
| 3,284,902 | A * | 11/1966 | Dillberg et al. | 433/7 |
| 3,835,540 | A * | 9/1974 | Biederman | 433/7 |
| 4,200,979 | A * | 5/1980 | Wallshein | 433/7 |
| 4,323,345 | A * | 4/1982 | Wallshein | 433/7 |
| 4,571,177 | A * | 2/1986 | Dahan | 433/7 |
| 5,167,500 | A * | 12/1992 | Miura | 433/7 |
| 5,281,133 | A * | 1/1994 | Farzin-Nia | 433/7 |
| 5,439,377 | A * | 8/1995 | Milanovich | 433/7 |
| 5,472,344 | A * | 12/1995 | Binder et al. | 433/7 |
| 6,482,001 | B2 * | 11/2002 | Farzin-Nia et al. | 433/7 |
| 6,499,996 | B2 * | 12/2002 | Forster | 433/7 |
| 6,644,967 | B2 * | 11/2003 | Ceppatelli et al. | 433/7 |
| 6,783,361 | B2 * | 8/2004 | Huge et al. | 433/7 |
| 7,074,036 | B1 * | 7/2006 | Keles | 433/7 |
| 2001/0036614 | A1 * | 11/2001 | Farzin-Nia et al. | 433/7 |
| 2002/0001789 | A1 * | 1/2002 | Forster | 433/7 |
| 2002/0018978 | A1 * | 2/2002 | Triaca et al. | 433/7 |
| 2002/0142259 | A1 * | 10/2002 | Ceppatelli et al. | 433/7 |
| 2003/0091952 | A1 * | 5/2003 | Bowman et al. | 433/18 |
| 2003/0207225 | A1 * | 11/2003 | Huge et al. | 433/7 |
| 2004/0152033 | A1 * | 8/2004 | Collins, Jr. | 433/7 |
| 2004/0214126 | A1 * | 10/2004 | Forster et al. | 433/7 |
| 2005/0037313 | A1 * | 2/2005 | Huge et al. | 433/7 |

* cited by examiner

*Primary Examiner*—Cris Rodriguez
*Assistant Examiner*—Sunil K. Singh
(74) *Attorney, Agent, or Firm*—Philip G. Meyers

(57) ABSTRACT

An orthodontic force mechanism includes a jack screw having a pair of ends, at least one of which is threaded, and a central spindle between the ends, which spindle has two intersecting radial through-holes therein. A pair of nut housings are mounted on the end portions of the jack screw, at least one of which is threadedly coupled to a threaded end portion of the jack screw. A lock mechanism mounted on the central spindle section includes a spring-loaded detent configured to engage an end opening of each of the through holes in the spindle when the through hole is in alignment with the detent, such that the spindle cannot rotate relative to the lock mechanism when the detent is inserted into a through hole. The detent can be moved out of engagement with a through hole using a tool inserted into that through hole from its opposite end.

10 Claims, 4 Drawing Sheets

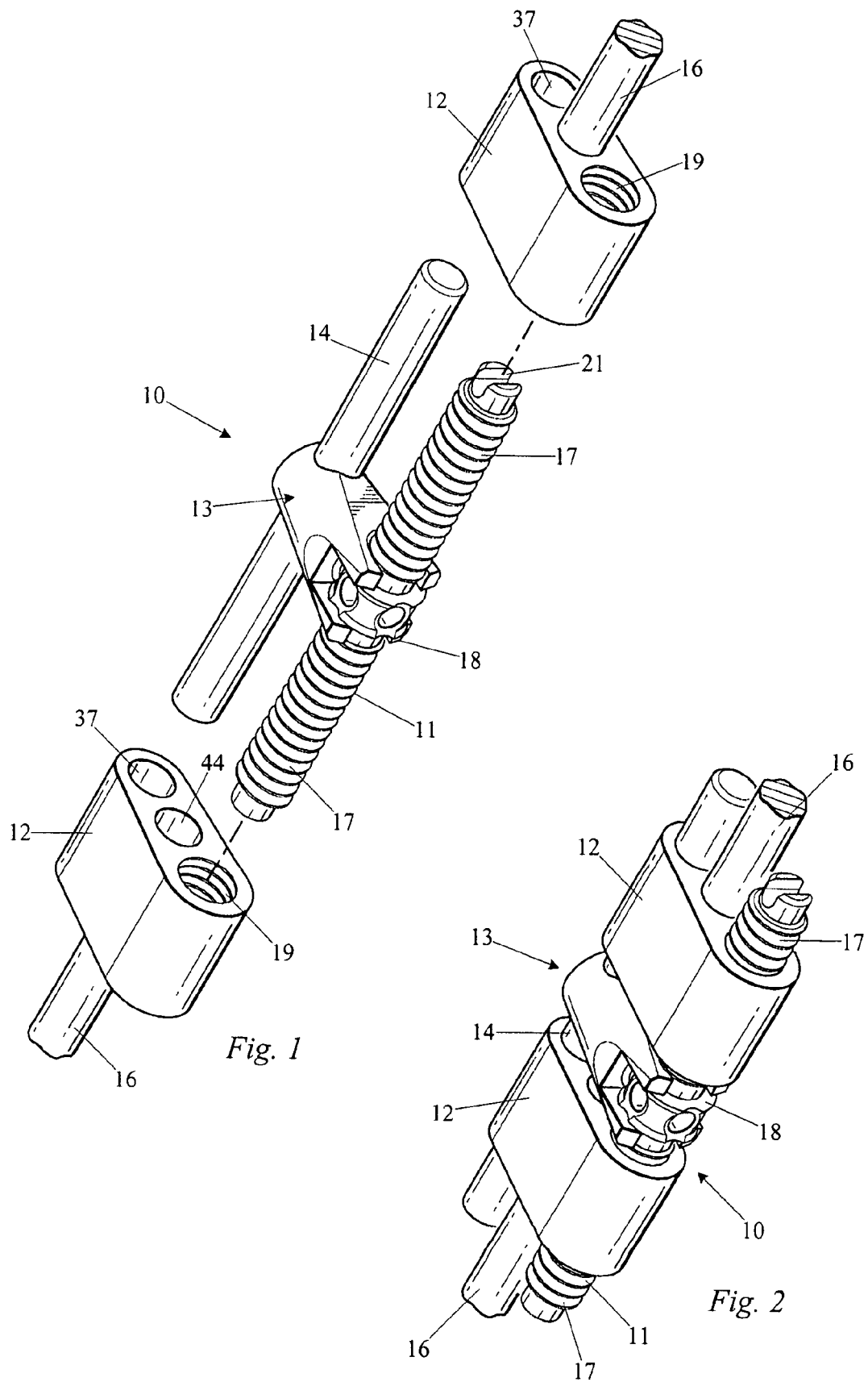

ORTHODONTIC FORCE MODULE

FIELD OF THE INVENTION

The present invention generally relates to orthodontics and, more particularly, to an orthodontic force modules of the type used for palatal expansion and other applications.

BACKGROUND OF THE INVENTION

Orthodontic palatal expansion is commonly carried out using a force module that is installed on the upper dental arch of a patient's mouth, the force module being connected to a palatal expander of a type commonly known in the art. The method of palatal expansion using expansion screws has become known in the art as "rapid palatal expansion" (RPE). Force modules used for this purpose must be tightened periodically to be effective.

Huge et al. U.S. Pat. No. 6,783,361, Aug. 31, 2004, describes an orthodontic mechanical force module having a jack screw whose rotation is controlled by a ratchet. In one embodiment, a pair of housings are interconnected with the patient in any appropriate manner, and are further rotatably interconnected with a rotatable spindle. At least one of these housings is also threadedly engaged with the spindle. A ratchet is associated with the spindle to selectively allow the spindle to rotate only in a direction that increases a magnitude of the treatment forces being exerted on the patient by changing the spacing between the pair of housings by a movement of at least one of the housings along the spindle due to its rotation. In an active position, the ratchet precludes the spindle from rotating in a direction that would tend to reduce the magnitude of the treatment forces being exerted on the patient.

The Huge et al. device, and also an appliance described in literature as the "RatchetRax" claim to provide bi-directional adjustment capability. The device of the present invention incorporates a mechanical locking device, unlike those of the previously mentioned devices, that allows bi-directional activation of the screw-mechanism without a multitude of tools or augmented instruction to the user. The RatchetRax is bi-directional, but moves only one nut body to create the expansion. The great disadvantage inherent with movement of one nut body as opposed to both nut bodies is that the overall lateral size of the single body movement device must necessarily be twice as wide to effect the same amount of expansion or contraction. Appliance size is critical relative to accommodation in the mouth and to patient comfort and tolerance.

Bi-directional adjustability allows the mechanism to be employed not only as an expansion device (activation of the nut bodies apart from each other) but also as a contraction device wherein the bodies are purposefully installed in the patient screwed apart and then activated to bring them together, thereby delivering a closing force as opposed to an expanding or opening force. This is a common application of such force modules, i.e. to move teeth adjacent to an edentulous space together to eliminate the space and mitigate the need for a prosthesis. The most common applications of such force modules are expansion of the palate, expansion of the mandibular alveolus, contraction of teeth adjacent to an edentulous site, and contraction of the palate.

Screw de-activation (screw reverses direction after activation) has always been a challenge with expansion screws. In order to control screw reversal, most prior art mechanisms have incorporated some type of screw thread drag adjunct (lacquer coating, nylon bushing, etc.). These have sometimes been successful, but many times not. A popular device described in U.S. Pat. No. 6,482,001 suffered problems with screw reversal that could not be controlled. When an expansion device fails, its removal and replacement subjects the patient to the rigors of duplicating previous protocols. Additionally, after such expansion has begun and then fails, appliance removal is considerably more uncomfortable because the involved tissues are in a heightened state of irritability. Furthermore, clinicians experience aggravation over lost time, duplication of effort, and poor public relations that invariably result from patients and/or parents of patients exasperated about the inconvenience of repeated appointments and delayed treatment time. Locking the screw in place mechanically is the surest way to prevent screw reversal. The present invention inhibits screw reversal without requiring additional tooling and instruction.

SUMMARY OF THE INVENTION

An orthodontic force mechanism according to the invention includes an elongated jack screw having at a pair of end portions, at least one of which is threaded, and a central spindle section between the end portions, which spindle section has at least two radial holes therein. A pair of nut housings are mounted on the end portions of the jack screw, at least one of which is threadedly coupled to a threaded end portion of the jack screw. A lock mechanism is mounted on the central spindle section, which lock mechanism includes a spring-loaded detent configured to engage an end opening of each of the radial holes in the spindle section when such hole is in alignment with the detent, such that the spindle cannot rotate relative to the lock mechanism when the detent is inserted into a radial hole, and is free to rotate relative to the lock mechanism when the detent is clear of a radial hole. In a preferred embodiment, the radial holes comprise intersecting through holes. The detent can be moved out of engagement with a through hole using a tool inserted into that through hole from its opposite end, such that a distal end of the tool pushes the detent out of the through-hole, and the same tool can then be used to rotate the jack screw. For the reasons noted above, it is preferred that both end portions of the jack screw are threaded in opposite directions, with the nut housings are threadedly coupled to the end portions of the jack screw.

In a preferred embodiment, the lock mechanism according to the invention comprises a housing having an outwardly opening recess and a bearing surface in engagement with the jack screw. The spring is disposed in the recess and confined for compression between the detent and the housing. A guide rod is slidably disposed in guide openings in each of the nut housings, and the housing of the lock mechanism is secured to the guide rod such that the lock mechanism does not rotate relative to the jack screw when the jack screw is rotated in a manner effective to cause the nut housings to move toward or away from one another. For this purpose, the housing of the lock mechanism can be slidably supported on the guide rod, or the guide rod can be made integral with the housing, e.g. as projections extending in opposite directions. A pair of attachment rods extend from each of the nut housings, which attachment rods are configured for attachment to an orthodontic appliance to be installed in the mouth of a patient.

In an especially preferred embodiment, the openings of each through hole in the spindle section are configured to receive a coil-spring activated detent element oriented perpendicularly to the long axis of the jack screw either within the confines of a lock housing, thereby "locking" and "unlocking" according to compression or expansion of the encapsulated coil spring. The detent element/lock housing interface with lock-seats of the spindle section inhibit the spindle from spontaneously rotating in a direction that would decrease the magnitude of desired force, but that, in fact, will readily without adjunct tooling or instruction allow reverse rotation of the spindle according to the need and desire of the prescribing clinician. A force module such as described in Huge et al. provided with a tempered leaf spring locking mechanism is prone to breakage as a result of binding with the plurality of activating tools. In the "RatchetRax" device, if after partial activation and bowing of the leaf spring, the direction is reversed against the "bow" of the spring, a binding force can occur thereby causing the leaf spring to break. A sliding ball or cup locking arrangement of the present invention is activated by a coil spring as opposed to a leaf spring, which coil spring is protected from all outside destructive influences by virtue of its encapsulation within the confines of the lock housing thereby rendering it more protected and hence less sensitive to mechanical breakage. Furthermore, the nature of a coil spring as it functions through a cycle of expansion and contraction is not stressed and therefore not prone to break like a "bowed" leaf spring is if in mid-cycle the direction of stress is reversed.

The invention further provides a lighted wrench for use in tightening an orthodontic force module. Such a wrench includes a hollow handle, a battery disposed in the handle, a head connected to the handle by a pivot, an LED mounted on the head and connected to the battery by electrical connections such as wires, and a tool mounted on the head proximate the LED and extending forwardly therefrom. The tool has a reduced diameter tip configured to fit inside a hole in a jack screw forming part of an orthodontic force module. These and other aspects of the invention are discussed further in the detailed description that follows.

BRIEF DESCRIPTION OF THE DRAWING

In the accompanying drawing, wherein like numerals represent like elements:

FIG. 1 is a perspective view of a force module according to the invention, with nut housings detached;

FIG. 2 is a perspective view of the force module of FIG. 1, with the nut housings threaded on;

DETAILED DESCRIPTION

Figure 3:
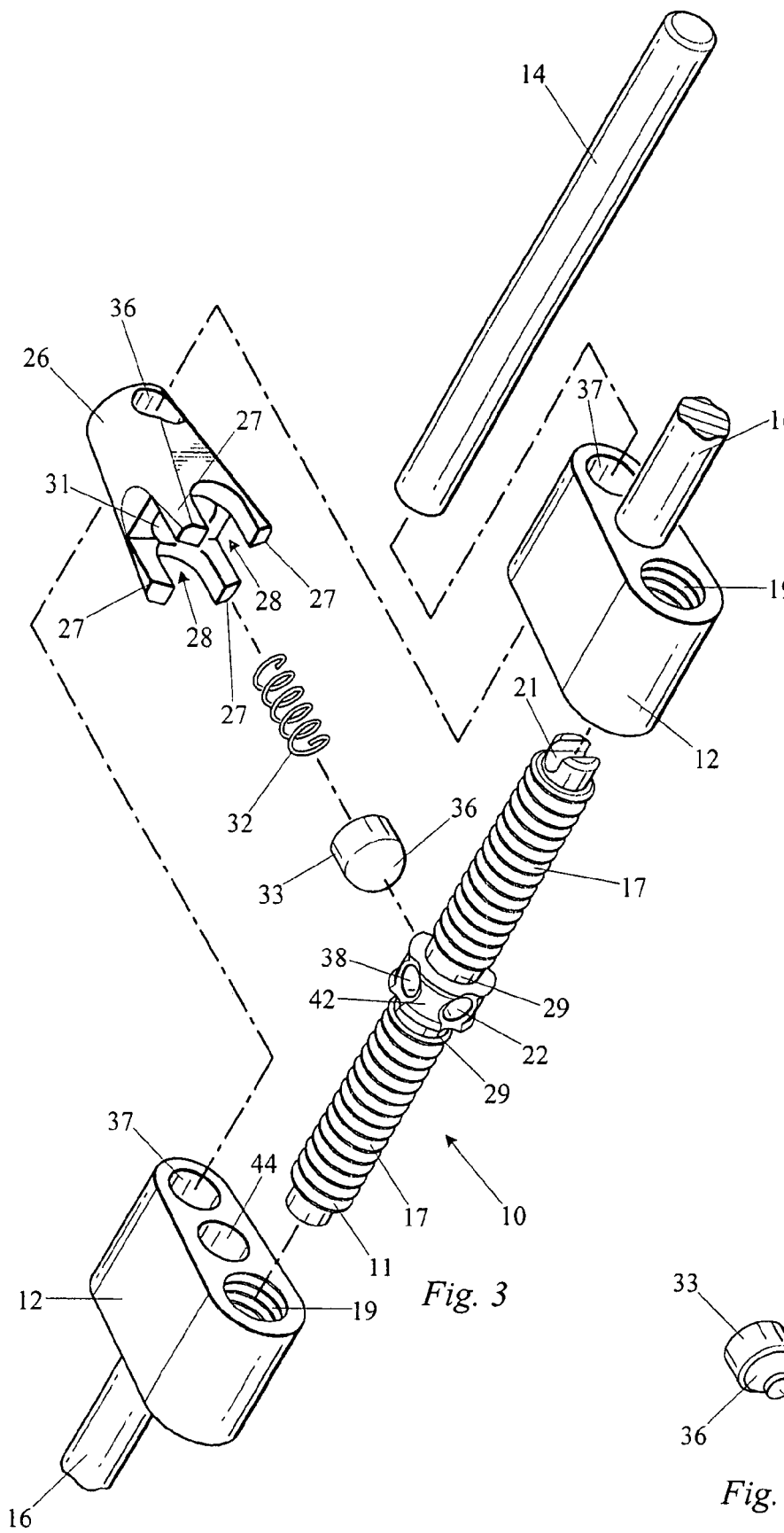
FIG. 3 is an exploded perspective view of the force module of FIG. 1.

The force module according to the invention has two main applications. In a first application, the nut housings are as proximate as possible and the desired result is to create a wider separation of anatomical entities, e.g., rapid palatal expansion. The main body of the device in its closed state is centered over the midline of a patient's palate with a clearance of some few millimeters with the lateral rods connected at their distal ends either by welding, brazing, or some other mechanical interface to the lingual surface of "bands" (braces) on a single tooth or multiple teeth on each side of the jaw. The end result of the expansion protocol is to open the suture joint which runs in the midline of the palate thereby separating one side from the other thus creating a greater inter-dimensional width between the teeth supporting the device. Activation is achieved by progressively rotating the jack screw in a direction to cause the device body or bodies to move apart from each other. Such activation is accomplished using a tool which inserts into holes in the center unthreaded portion of the jack screw spindle. Frequency of activation is monitored and controlled under the auspice of a qualified and licensed health care provider. Such activation continues according to a prescribed schedule until the desired expansion has been accomplished.

In the second application, the device is adjusted so that nut bodies are maximally separated prior to fabrication of the patient assembly before insertion into the mouth. The desired end result in this application could be the closing of space created by a missing tooth, or as an adjunct to resolve a "Brody Bite". The device would be activated so that the opposing nut bodies would come together. For instance, the lateral rods would be attached at their distal ends to each of the teeth adjacent to an edentulous site. The treatment goal is to deliver the necessary force required to move the teeth toward each other until they are in contact thereby eliminating the space and mitigating the need for a prosthesis to replace the missing dental unit. In a Brody Bite treatment, the device would be applied to effect a result just opposite that described in the first application above. In both applications as noted above, the device would function in one of or multiples of the hereinafter described mechanisms all designed to inhibit screw reversal.

Referring to FIGS. 1-4, a force module 10 according to the invention includes a jack screw 11, a pair of nut housings or bodies 12, a lock mechanism 13 supported on a guide rod 14, and a pair of attachment rods 16 which may be welded or otherwise secured to nut housings 12 for connecting force module 10 to other orthodontic components that engage the anatomy, such as for the purposes discussed above. Jack screw 11 has a pair of threaded end portions 17 separated by a central spindle section 18. End portions 17 are essentially identical (Class 3a 2-56 UNC) except that they are threaded in opposite directions so that rotation of jack screw 11 moves nut housings either closer together or further apart along the length of jack screw 11. In a preferred embodiment, jack screw 11 is approximately 0.60" to 0.80" long depending on the application.

Each nut housing 12 has a threaded through-hole 19 into which one of threaded end portions 17 is coupled. Nut housings 12 are, for example, identically threaded Class 3a 2-56 UNC, except that one has a right hand internal thread and the other has a left hand internal thread. One end portion 17 of jack screw 11 terminates in a notch 21 that allow jack screw to be screwed or unscrewed with a screwdriver.

FIG. 2 illustrates force module 10 with nut housings 12 brought close together by repetitive tightening of jack screw 11 as described hereafter. It is possible according to the invention that only one end portion 17 be threaded, and in such a case the other end portion will be welded or otherwise fixed to the other nut housing. This is, however, not preferred because a one-sided jack screw renders the force module not as compact as one capable of extending the same distance using a double-sided jack screw.

Spindle section 18 of jack screw 11 is unthreaded and is of greater diameter than the threaded end portions 17. Spindle section 18 has two 90° opposed, intersecting through holes 22 therethrough that receive the activation tool thereby facilitating rotation of the jack screw 11.

Although there are four activation hole openings in the example shown, only one hole at a time lends itself to activation of the jack screw. That hole is 180° opposed to the hole that is locked in position by the lock mechanism 13.

Referring to FIG. 3, lock mechanism 13 comprises a lock housing 26 having two pairs of arms or tines 27 that define a pair of spaced, laterally opening, rounded U-shaped grooves 28 that match the curvature of jack screw 11. When mounted on jack screw 11, arms 27 engage a pair of annular shoulders 29 on opposite sides of central spindle section 18. Jack screw 11 is thereby rotatably mounted in grooves 28. Lock housing 13 further has a central hollow portion or recess 31 that opens in the same direction as grooves 28. A compression coil spring 32 is disposed in recess 31 with its inner end engaging the bottom of recess 31. A detent or lock element 33 takes the form of a rearwardly-opening cup with a rearwardly facing recess 34 and a rounded outer end 36. Spring 32 fits inside recess 31 and biases detent 33 towards a projecting position. The hollow portion of recess 31 thus encapsulates the mesial end of coil spring 32, which exerts a constant expansive pressure. The cup-shaped lock element 33 can fit entirely within the larger diameter recess 31 of lock housing 26, free to slide parallel to the long axis of housing 26 to thereby accomplish the locking/unlocking function.

Housing 26 further has a transverse through hole 36 that guide rod 14 slides into. The form of lock housing 26 is such that it is stabilized in place relative to the spindle of jack screw 11. To hold lock mechanism 13 so that it does not rotate when jack screw 11 is rotated, lock housing 26 is centered on guide rod 14, and the ends of guide rod 14 are retained in a pair of opposed holes 37 in nut housings 12. Holes 37 are spaced from and extend in parallel to the threaded through-holes 19. Guide rod 14 passes through hole 36 in housing 26 and may be welded or integrally formed with housing 26 so that the ends of the guide rod 14 remains equidistant from housing 11 during travel of the nut bodies 12. Guide rod 14 passes through holes 37 in nut bodies 12, which move freely along rod 14 as nut bodies 12 are moved apart or together. The primary purpose of rod 14 is to support the distal end of lock housing 26. Arms 27 and guide rod 14 maintain the housing 26 stationary relative to the jack screw 11 so that the lock element 33 is prohibited from leaving its centered position over the through holes 22 that would otherwise occur as the housing 11 would be influenced by the turning spindle to follow the direction of rotation.

Figure 4:
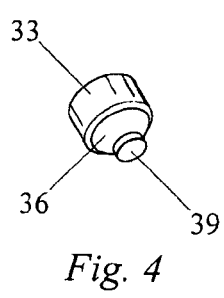
FIG. 4 is a perspective view of an alternate form of detent element according to the invention.
Figure 5A:
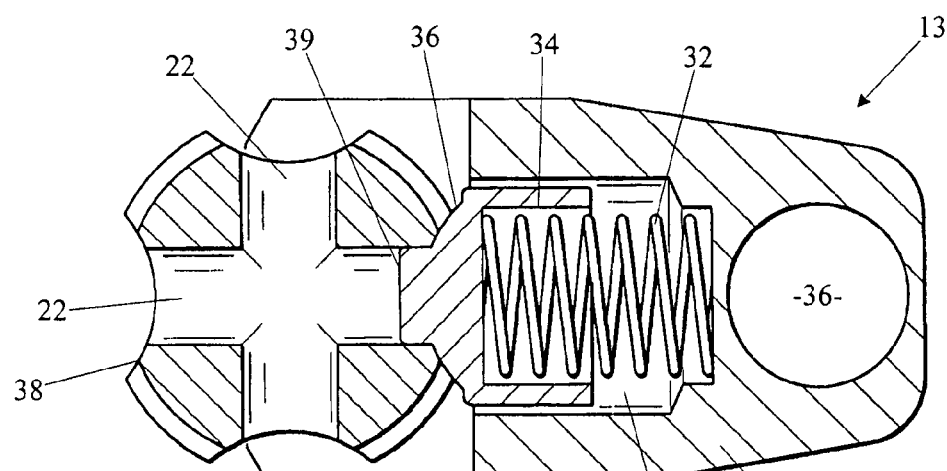
FIGS. 5A, 5B and 5C are a series of lengthwise sectional views showing use of a tool according to the invention to unlock the lock mechanism and rotate the jack screw.
Figure 5B:
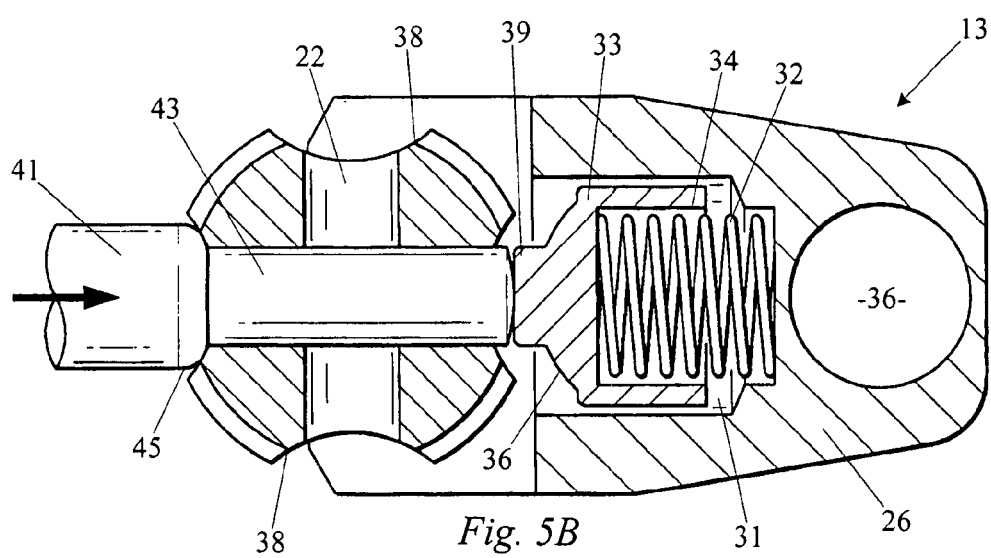
Figure 5C:
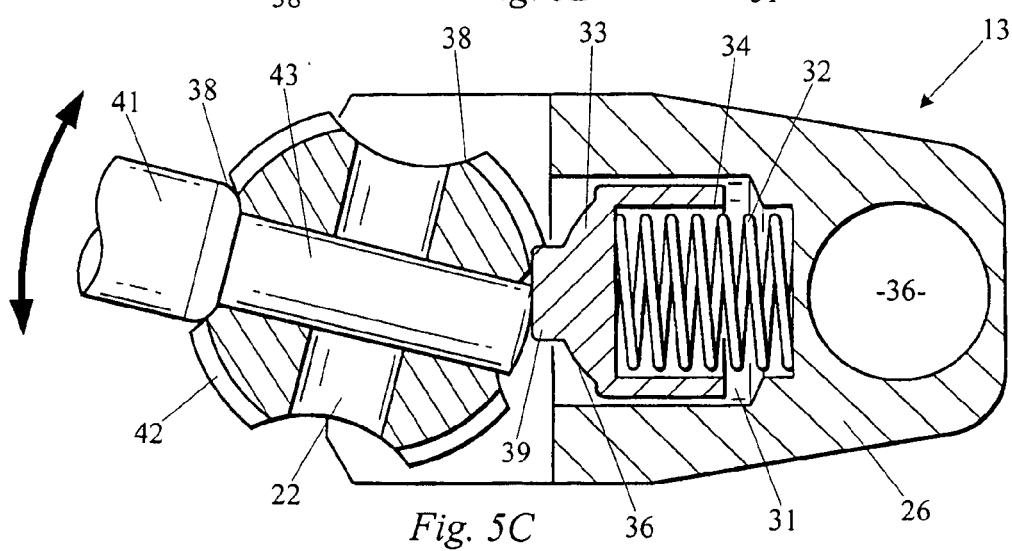

FIGS. 5A-5C illustrate lock mechanism 13 in operation. As shown in FIG. 5A, end portions of each through hole 22 are flared to form lock seats 38 in the form of countersunk holes that match the curvature of rounded end 36 of detent 33. Preferably, as shown in FIG. 4, detent 33 has a cylindrical tip 39 that fits loosely into hole 22 just behind lock seat 38 to provide a more secure locking action. When detent 33 is in alignment with a hole 22 in spindle section 18, spring 32 biases it into contact with lock seat 38 as shown, locking spindle section 18 from rotation. A wrench or similar tool 41 is inserted into the hole 22 that detent 33 has engaged, but from the opposite end as shown. Tool 41 contacts the tip of rounded end 36 and pushes it back, compressing spring 32. The user then rotates jack screw 11 using tool 41 by an angle equal to the angular spacing of holes 22, in this example 90 degrees. As the user moves tool 41 and jack screw 11 through the angle, rounded end 36 engages and slides along a rounded circumferential groove 42 in spindle section 18 (FIG. 5C) that serves as a race for the locking element. If a locking element as shown in FIG. 4 is used, groove 42 has an annular, central bottom channel matching the profile of tip 39 for tip 39 to slide in.

When detent 33 is brought into alignment with the next hole 22, it engages its seat 38 and assumes a position like that shown in FIG. 5A. Tool 41 is then withdrawn and reinserted into the next hole 22 if further tightening (or loosening) of force module 10 is desired. During these steps, nut housings 12 move further apart or closer together depending on the direction of rotation of the jack screw. In the case of palatal expansion, nut housings 12 are periodically moved further apart so that attachment rods 16 apply additional force to the portions of the device that engage the teeth. Rods 16 may be permanently or removably installed in a third set of holes 44 in nut housings 12.

As tool 41 rotates with the spindle section 18, contact with the lock element 33 is lost. As lock element 33 transitions away from the end of the tool 41, it rotates into contact with and is supported by the spindle race, groove 42. When the spindle completes a 90 degree arc, the lock element 33 eventually loses contact with the race 42 and falls into the next spindle lock seat 38, thus forming the next lock. Therefore, in this embodiment, a lock cycle will always amount to one 90 degree turn of the spindle 18.

Tool 41 in the preceding embodiment is a 0.080"diameter wire the end of which has been reduced in diameter, e.g., to 0.035". The end section extends approximately 0.1"from the end of a 0.040"radius transition of the .080"diameter section to the .035"diameter section. Total length is about 2 inches, with the distal end formed to mate with a handle to facilitate manipulation and make large enough that it cannot be dropped down the patient's throat. The radiused shoulder 45 of tool 41 is configured to act as a stop as it engages the rounded lock seat 38, ensuring that its narrow tip 43 is inserted to the proper depth as shown in FIGS. 5A-5C.

A number of variations of the arrangement shown in FIGS. 1-5 are possible. Although a pair of intersecting holes 22 is shown, it is possible to use a plurality of blind radial holes instead and rely on tool 41 to cause the lock element to unseat by force, rather than by engaging it directly, as would be possible with the lock element lacking tip 39 as shown in FIGS. 1-3. In the event holes 22 are relatively shallow such that tool 41 as described above could not be used, the spindle section could be provided with flats, such as by giving it an octagonal shape in cross section. The wrench would then be configured to engage these flats. The use of a guide rod 14 is preferred, but it is possible to make the lock housing integral with, or rigidly connected to, one of the nut bodies 12 instead. As a result, only one nut body would be movable and the device would suffer the same disadvantages as known one-sided jack screw devices.

Force module 10 of the invention is commonly mounted near the roof of the mouth, a dark and difficult to access location. Holes 22 are small and difficult to see. For that reason, an improved tool 50 according to the invention includes the tool 41 having a rod-shaped end that fits into holes 22, and a much larger lighted handle behind it. In the embodiment shown in FIG. 6, a proximate end of tool 41 is mounted on one side of a head 52 of tool 50. A light emitting diode 53 is mounted at the front of head 52. Head 52 is connected to a handle 51 by a pivot 54 that allows the user to reposition head 52 and tool 41 as needed. Handle 51 is longer and several times wider than the corresponding handle portion of tool 41 as discussed above. Pivot 54 may be of the type requiring considerable force to shift between incremental positions, allowing tool 41 to remain stable during use with head 52 in the desired position. LED 53 is powered by a battery 56 inside handle 51 and connected thereto by wires 57. A lanyard eyelet 58 or similar attachment device may be provided at the end of handle 51 opposite head 52. Tool 41 is typically made from stainless steel or the like, but handle 51, head 52 and pivot joint 54 could be made from molded plastic parts. Eyelet 58 may connect directly to an end cap that unscrews to allow changing of battery 56 when needed.

Figure 6:
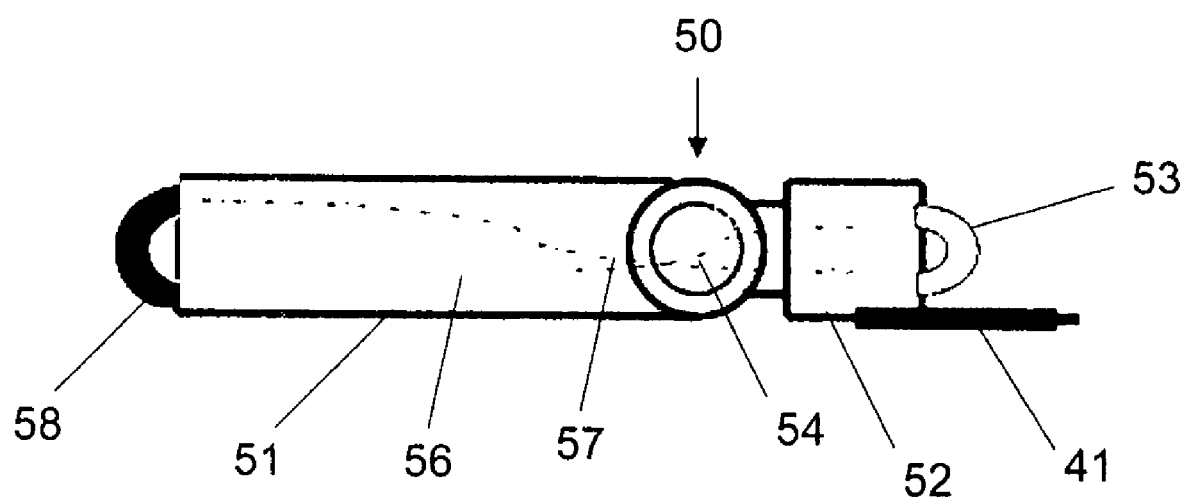
FIG. 6 is a side view of a lighted tool according to the invention.

In the straight configuration shown in FIG. 6, the tool of "light wrench" 50 is advanced toward the through-hole 22 of the spindle. In situ near the roof of the mouth, the opening of through-hole 22 points straight toward the front of the mouth, so as the wrench 50 is advanced toward the hole 22, the light from LED 53 illuminates the darkness of the mouth and the hole, thus facilitating insertion of the wrench end into the hole. In this configuration, the user is able to press the wrench 41 against the lock element 33, thereby pushing it out of and away from its seat in the lock seat 38 of the spindle.

Pivot 54 preferably permits head 52 to swing up to 90 degrees in either direction from the position shown. This swiveling is necessary to allow an appropriate 90° rotation of the spindle. If there were no swivel, the entire light/wrench assembly would need to rotate 90°, which would be impossible since the light/wrench overall length would exceed the distance the patient would be able to open the mouth to allow such rotation. After the lock element has been displaced, the user applies a motion which, while holding pressure against the lock element, causes the light/wrench to "gable" at the joint, thus beginning the rotation of the spindle until complete at 90°. The present invention contemplates a method of using the tool 50 according to the invention as described above, either with the bi-directional force module of the invention or with other compatible force modules.

While certain embodiments of the invention have been illustrated for the purposes of this disclosure, numerous changes in the method and apparatus of the invention presented herein may be made by those skilled in the art, such changes being embodied within the scope and spirit of the present invention as defined in the appended claims.

The invention claimed is:

1. An orthodontic force mechanism, comprising:
   an elongated jack screw having a pair of end portions, at least one of which is threaded, and a central spindle section between the end portions, which spindle section has at least two radial holes therein;
   a pair of nut housings mounted on the end portions of the jack screw, at least one of which is threadedly coupled to a threaded end portion of the jack screw; and
   a lock mechanism mounted on the central spindle section, which lock mechanism includes a detent configured to engage an end opening of each of the radial holes in the spindle section when such hole is in alignment with the detent, such that the spindle cannot rotate relative to the lock mechanism when the detent is inserted into a hole, and is free to rotate relative to the lock mechanism when the detent is clear of a hole, wherein the detent can be moved out of engagement with a hole using a tool inserted into that hole from its opposite end such that a distal end of the tool pushes the detent out of the hole, wherein the lock mechanism comprises a housing having an outwardly opening recess and a bearing surface in engagement with the jack screw, wherein a spring is disposed in the recess and confined for compression between the detent and the housing.

2. The orthodontic force mechanism of claim 1, further comprising a mechanism connecting the lock mechanism to the nut housings in a manner effective to prevent the locking mechanism from moving with the spindle section during rotation of the jack screw with a tool.

3. The orthodontic force mechanism of claim 1, wherein the end portions of the jack screw are threaded in opposite directions, and the nut housings are threadedly coupled to the end portions of the jack screw.

4. The orthodontic force mechanism of claim 1, wherein the lock mechanism comprises a housing having an outwardly opening recess and a bearing surface in engagement with the jack screw, and the spring is disposed in the recess and confined for compression between the detent and the housing, and the mechanism further comprises a guide rod slidably disposed in guide openings in each of the nut housings, wherein the housing of the lock mechanism is secured to the guide rod such that the lock mechanism does not rotate relative to the jack screw when the jack screw is rotated in a manner effective to cause the nut housings to move toward or away from one another.

5. The orthodontic force mechanism of claim 1, wherein the radial holes comprise a pair of through holes that intersect at a lengthwise axis of the jackscrew.

6. The orthodontic force mechanism of claim 5, wherein the spindle section has two of the through-holes therein, which through-holes perpendicular to each other.

7. The orthodontic force mechanism of claim 1, wherein the detent comprises a cup having a rounded outer end surface on that engages end openings of the radial holes, and an inner recess into which the spring extends.

8. The orthodontic force mechanism of claim 7, wherein the outer end openings of the radial holes are flared and rounded to form lock seats with a curvature that complements the curvature of the rounded outer end surface of the detent.

9. The orthodontic force mechanism of claim 1, further comprising a pair of attachment rods extending from each of the nut housings, which attachment rods are configured for attachment to an orthodontic appliance to be installed in the mouth of a patient.

10. An orthodontic force mechanism, comprising:
    an elongated jack screw having a pair of end portions threaded in opposite directions and a central spindle section between the end portions, which spindle section has at least two intersecting radial through-holes therein;
    a pair of nut housings threadedly coupled to the end portions of the jack screw;
    a pair of attachment rods extending from each of the nut housings, which attachment rods are configured for attachment to an orthodontic appliance to be installed in the mouth of a patient;
    a lock mechanism mounted on the central spindle section, which lock mechanism includes a detent configured and loaded by a compression spring to engage an end opening of each of the through holes in the spindle section when such through hole is in alignment with the detent, such that the spindle cannot rotate relative to the lock mechanism when the detent is inserted into a through-hole, and is free to rotate relative to the lock mechanism when the detent is clear of a through hole, wherein the detent can be moved out of engagement with a through hole using a tool inserted into that through hole from its opposite end such that a distal end of the tool pushes the detent out of the through-hole;
    wherein the lock mechanism comprises a housing having an outwardly opening recess and a bearing surface in engagement with the jack screw, wherein the compression spring is disposed in the recess and confined for compression between the detent and the housing; and a guide rod slidably disposed in guide openings in each of the nut housings, wherein the lock mechanism is secured to the guide rod such that the lock mechanism does not rotate relative to the jack screw when the jack screw is rotated in a manner effective to cause the nut housings to move toward or away from one another.

* * * * *